United States Patent [19]

Tananier et al.

[11] 4,275,193
[45] Jun. 23, 1981

[54] 4,5-CARBAMATES OF FORTIMICIN B

[75] Inventors: John S. Tananier; Jerry R. Martin, both of Waukegan, Ill.

[73] Assignee: Abbott Laboratories, North Chicago, Ill.

[21] Appl. No.: 79,134

[22] Filed: Sep. 26, 1979

[51] Int. Cl.³ .......................................... C07D 413/12
[52] U.S. Cl. ................................. 536/17 R; 424/180; 548/221
[58] Field of Search ........................ 548/221; 424/180; 536/17 B

[56] References Cited

U.S. PATENT DOCUMENTS

| | | | |
|---|---|---|---|
| 4,065,616 | 12/1977 | Umezawa et al. | 536/18 |
| 4,091,032 | 5/1978 | Tadanier et al. | 424/118 |
| 4,155,902 | 5/1979 | Tadanier et al. | 424/118 |
| 4,169,198 | 9/1979 | Martin et al. | 536/17 B |
| 4,169,942 | 10/1979 | Mochide et al. | 424/180 |
| 4,176,178 | 11/1979 | Martin et al. | 424/180 |

*Primary Examiner*—Mary C. Lee

*Attorney, Agent, or Firm*—Robert L. Niblack; Gildo E. Fato; Joyce R. Niblack

[57] ABSTRACT

Fortimicin B-4,5-carbamates represented by the formula:

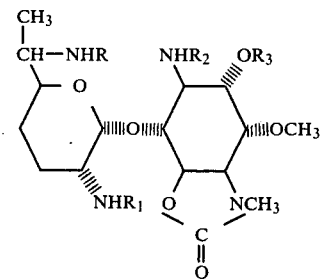

wherein R is hydrogen or an amine-protecting group; $R_1$ is hydrogen or an amine-protecting group; $R_2$ is hydrogen or loweralkoxycarbonyl; and $R_4$ is hydrogen or loweralkoxycarbonyl. The compounds are useful as intermediates in the preparation the 2-epi-fortimicins.

7 Claims, No Drawings

4,5-CARBAMATES OF FORTIMICIN B

BACKGROUND OF THE INVENTION

Aminoglycoside antibiotics have proven to be a valuable class of antibiotics which include the streptomycins, kanamycins, neomycins, gentamicins, tobramycins, amikacin and the more recently discovered fortimicins. As with other classes of antibiotics, chemical modification of the parent antibiotics has been found to advantageously alter either the pharmacological properties or the antibacterial properties of many of the naturally produced aminoglycoside antibiotics either by increasing their antibacterial spectrum, increasing their intrinsic activity, increasing their activity against resistant strains or providing compounds which are less toxic than the parent antibiotics.

Chemical modification has been found to be of value in the fortimicin family of antibiotics as well. See for example, U.S. Pat. Nos. 4,091,032; 4,207,314; 4,124,746; 4,192,867; 4,169,198; 4,183,920; 4,176,178; 4,187,296; 4,187,298; 4,187,297 and 4,187,299.

Another valuable modification is disclosed in commonly assigned, co-pending application Ser. No. 25,236 filed Mar. 29, 1979, now abandoned, which claims 2-epi-fortimicin A, 2-epi-fortimicin B and 2-epi-4-N-acyl and alkylfortimicin B derivatives. The present invention provides intermediates useful in the preparation of the 2-epi-fortimicins A and B.

SUMMARY OF THE INVENTION

The present invention provides 4,5-carbamates of fortimicin B. The compounds are useful as intermediates in the preparation of the antibiotic 2-epi-fortimicin B.

DETAILED DESCRIPTION OF PREFERRED EMBODIMENTS

The 4,5-carbamates of fortimicin B of the present invention are represented by the formula:

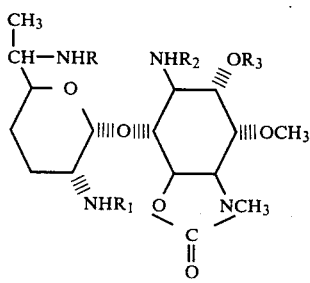

wherein: R is hydrogen or an amine-protecting group; $R_1$ is hydrogen or an amine protecting group; $R_2$ is hydrogen or loweralkoxycarbonyl; and $R_3$ is hydrogen; and when R, $R_1$ or $R_2$ are hydrogen, the salts thereof.

The term "an amine protecting group" refers to monocyclicaryloxycarbonyl groups such as benzyloxycarbonyl, 2-bromobenzyloxycarbonyl, 2-chlorobenzyloxycarboxyl, etc. The preferred amine protecting group is benzyloxycarbonyl.

The term "loweralkoxycarbonyl" refers to such groups having from 1 to 6 carbon atoms in the alkoxy radical, ie. methoxycarbonyl, ethoxycarbonyl, etc.

The preferred group is methoxycarbonyl.

The preparation of the intermediates of this invention is detailed in the following examples and summarized in the following reaction schemes.

Generally speaking, the carbamates of this invention are used in the preparation of 2-epi-fortimicin B as follows. A 4,5-carbamate of fortimicin B is converted to the corresponding 2-O-methanesulfonate. Solvolysis of the latter in aqueous 1,2-dimethoxyethane in the presence of ammonium acetate yields the protected 2-epi-carbamate and bis-carbamate in equimolar mixtures.

Alternatively, when solvolysis of the 2-O-methanesulfonate derivative is carried out in a mixture with aqueous tetrahydrofuran and sodium bicarbonate, the 2-epi-oxazoline is formed. When the latter is heated under reflux in a solution prepared from ammonium acetate and aqueous 1,2-dimethoxyethane, an approximately equimolar mixture of 2-epi-4,5carbamate and the 2-epi-bis-carbamate is formed.

The mixture of 2-epi-mono and biscarbamates may then be separated into the pure components by chromatography. Alternatively, the mixture can be heated under reflux with a mixture of sodium bicarbonate and methanol and the monocarbamate converted the the bis-carbamate which may then be isolated by chromatography.

Hydrogenolysis of the resulting 1,2'-di-N-benzyloxycarbonyl-2-epi-fortimicin B-bis-carbamate with 5% Pd/C in the presence of 0.2 N-methanolic hydrochloric acid gives 2-epi-fortimicin B dihydrochloride which in turn is an intermediate in the preparation of 2-epi-fortimicin A and 2-epi-formimicin B derivatives as disclosed in co-pending commonly assigned patent application Ser. No. 25,236 filed Mar. 29. 1979, now abandoned.

Briefly, 2-epi-fortimicin B is converted to 1,2',6'-tri-N-benzyloxycarbonylfortimicin B with N-benzyloxycarbonyloxysuccinimide, following the general procedure described in U.S. Pat. No. 4,091,032. Catalytic hydrogenation of the resulting produts, tetra-N-benzyloxycarbonyl-2-O-[N-benzyloxycarbonylglycyl]-2-epi-formticin A and tetra-N-benzyloxycarbonyl-2-epi-fortimicin A, with 5% Pd/C in 0.2 N methanolic hydrochloric acid yields 2-O-glycyl-2-epi-fortimicin A and 2-epi-fortimicin A, respectively, isolated as their perhydrochloride salts.

Alternatively, fortimicin B is converted to tetra-N-acetylfortimicin B by known methods. Selective hydrolysis of the latter with sodium bicarbonate in aqueous methanol gives 1,2', 6'-tri-N-acetylfortimicin B which is converted to the corresponding 4-N-ethoxycarbonyl derivative which is then readily cyclized to the 4,5-carbamate in a refluxing suspension of sodium bicarbonate in aqueous methanol. Treatment of the carbamate with methanesulfonic anhydride in pyridine results in the 2-epi-1,2-oxazoline derivative of the carbamate and hydrolysis of the latter with aqueous hydrochloric acid in tetrahydrofuran results in 1,2',6'-tri-N-acetyl-2-epi-fortimicin B-4,5-carbamate. The latter is converted to the 2-O-benzyl ether with benzylbromide and barium hydroxide. Hydrolysis of the latter with aqueous sodium hydroxide resulted in 2-O-benzyl-2-epi-fortimicin B. Treatment of the latter with N-benzyloxycarbonyloxysuccinimide results in 1,2',6'-tri-N-benzyloxycarbonyloxy-2-epi- fortimicin B. Treatment of the latter with the N-hydroxysuccinimide ester of N-benzyloxycarbonylglycine results in tetra-N-benzyloxycarbonyl-2-O-benzyl-2-epi-fortimicin A which is converted to 2-epi-fortimicin A tetrahydrochloride as described above.

The preparation of the intermediates of this invention are summarized in the following reaction schemes:

$1507 \text{ cm}^{-1}$; $NMR(CDCl_3)$ $\delta 1.03$ ($C_{6'}$—$CH_3, J_{6'7'}=6.0$ Hz), $2.32(C_4$—$NCH_3)$, $3.41(OCH_3)$.

Analysis Calcd. for $C_{39}H_{50}N_4O_{11}$: C,62.39; H, 6.71; N,7.46; Found: C,62.16; H, 6.76; N,7.43

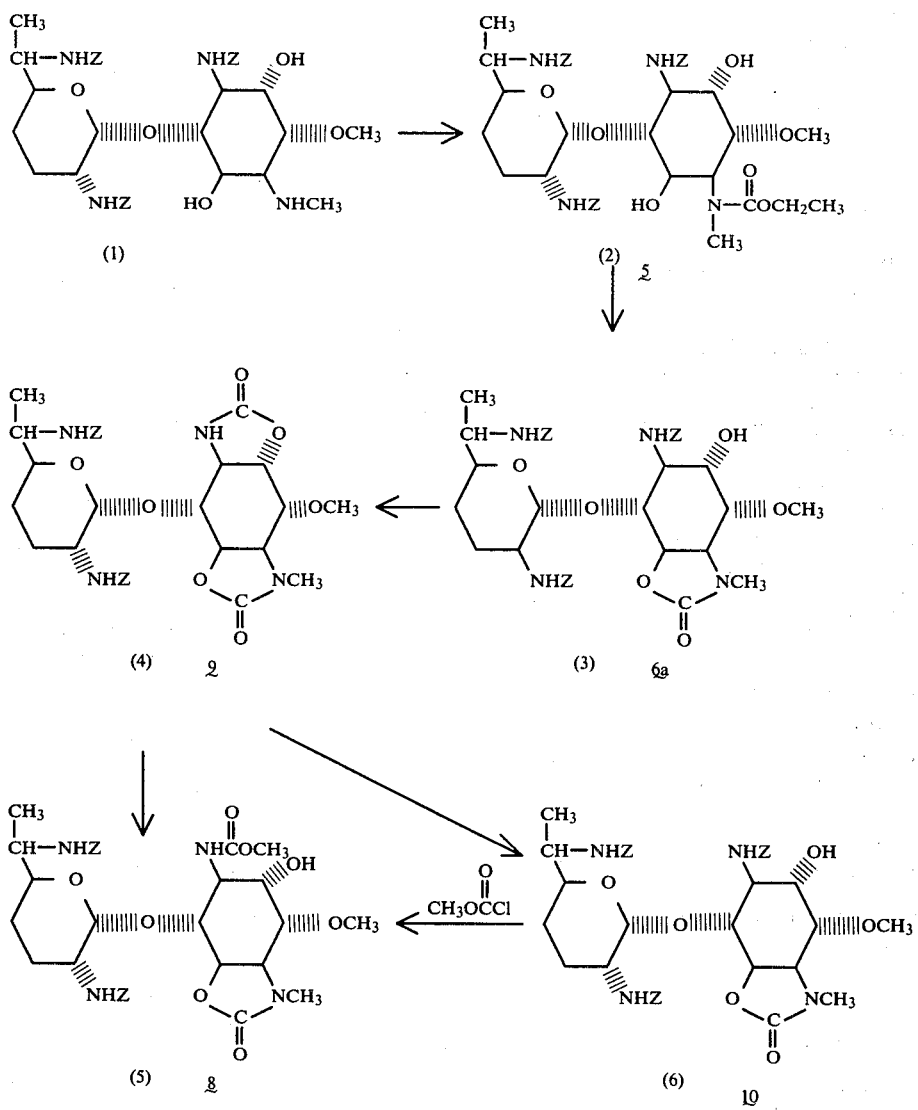

The following examples further illustrate the present invention.

EXAMPLE 1

1,2',6'-Tri-N-benzyloxycarbonylfortimicin B (1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° C. for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide [234:1.4:0.1(v/v/v)] gives 1.05 g of product (1): $[\alpha]_D^{25}$ $-16.5°$ (c 1.0, $CH_3OH$); $IR(CDCl_3)$ 1712 and

EXAMPLE 2

4-N-Ethoxycarbonyl-1,2',6'-tri-N-benzyloxycarbonylfortimicin B(2)

To a magnetically stirred solution of 3.02 g of 1,2',6'-tri-N-benzyloxycarbonylfortimicin B(1), 130 ml of methanol and 60 ml of a solution of 3.02 g of sodium bicarbonate in 72 ml of water is added 0.90 ml of ethyl chloroformate. Stirring is continued at room temperature for 3 hours. The major portion of the methanol is evaporated under reduced pressure and the residue is shaken with a mixture of 200 ml of chloroform and 200 ml of 5% aqueous sodium bicarbonate. The chloroform solution is separated and washed with 200 ml of water. The aqueous solutions are washed in series with four 100 ml portions of chloroform. The chloroform solutions are combined, and the chloroform is evaporated under reduced pressure leaving 3.36 g of white glass. The latter is chromatographed on 250 g of silica gel packed and eluted with benzene-methanol[85:15(v/v)] to yield 2.57 g of the desired product: NMR(CDCl$_3$) $\delta$1.15d(J=6.4 Hz)(C$_6'$—CH$_3$); 1.27 t(J=7.2 Hz)(OCH$_2$CH$_3$); 3.02(NCH$_3$); 3.43(NCH$_3$); IR(CDCl$_3$) 3555, 3437, 1707, 1658 cm$^{-1}$.

EXAMPLE 3

1,2',6'-Tri-N-benzyloxycarbonylfortimicin B-4,5-carbamate(3)

A solution of 13.0 g of 4-N-ethoxycarbonyl-1,2',6'-tri-N-benzyloxycarbonylfortimicin B(2), 5.3 g of sodium bicarbonate and 370 ml of methanol is heated under reflux for 1.5 hours. The methanol is evaporated under reduced pressure, and the residue triturated with chloroform. The chloroform suspensions are filtered. Evaporation of the chloroform from the filtrate leaves 12.1 g of product. The latter is chromatographed on 850 g of silica gel using a solvent system prepared from benzene-ethanol[9:1(v/v)] to yield 10.9 g of pure product(3):$[\alpha]_D^{22}$ +2.5° (c 1%,CH$_3$OH); NMR(CDCl$_3$)$\delta$0.98d(J=6.0 Hz)(C$_6'$—CH$_3$),2.83(NCH$_3$),3.44(OCH$_3$); IR(CDCl$_3$)3562, 3468, 3320, 1759, 1706 cm$^{-1}$.

EXAMPLE 4

2',6'-Di-N-benzyloxycarbonylfortimicin B-1,2:4,5-bis carbamate(4)

To a solution prepared from 1.02 g of the compound of Example 3 in 20 ml of dry N,N-dimethylformamide, magnetically stirred, under a nitrogen atmosphere and cooled in an ice bath, is added 0.280 g of 57% oily sodium hydroxide. Stirring is continued for 4 hours with ice bath cooling. Acetic acid(0.8 ml) is then added to the cold suspension. The resulting solution is shaken with a mixture of 100 ml of chloroform and 200 ml of 5% aqueous sodium bicarbonate. The chloroform solution is separated and washed with 200 ml of water. The aqueous solutions are washed in series with three 100 ml portions of chloroform. The chloroform solutions are combined and dried over magnesium sulfate. The chloroform is evaporated under reduced pressure and residual N,N-dimethyformamide is removed by co-distillation with toluene under reduced pressure leaving 1.05 g of a white glass. The latter product (1.01 g) is dissolved in 20 ml of pyridine and 2.0 ml of acetic anhydride is added. The resulting solution is kept at room temperature for 24 hours. The resulting solution is then shaken with a mixture of 200 ml of chloroform and 200 ml of 5% aqueous sodium bicarbonate. The chloroform solution is separated and washed with 200 ml of water. The aqueous solution is washed with three 100 ml portions of chloroform. The chloroform solutions are combined and the chloroform evaporated under reduced pressure. Residual pyrydine is removed by co-distillation with toluene under reduced pressure leaving 1.04 g of a white glass. The latter (1.01 g) is chromatographed on a column of 100 g of silica gel packed and eluted with a solvent system composed of 1,2-dichloroethane-ethyl acetate [14:16(v/v)]. Initial fractions yield 0.161 g of 1,2',6'-tri-N-benzyloxycarbonyl-2-O-acetylfortimicin B-4,5-carbamate. Further elution of the column yields 0.594 g of a white class which is rechromatographed on a column of 40 g of silica gel packed and eluted with a solvent system composed of methylene chloride-ethyl acetate [3:3(v/v)] to yield 0.398 g of product (4):$[\alpha]_D^{21}$ −2.33° (c 1%, CH$_3$OH); NMR(CDCl$_3$) $\delta$1.16d(J=7.0 Hz)(C$_6'$—CH$_3$),2.85(NCH$_3$),3.52(OCH$_3$); IR(CDCl$_3$) 3440, 3300, 1750, 1697 cm$^{-1}$.

EXAMPLE 5

1-N-Methoxycarbonyl]-2',6'-di-N-benzyloxcarbonyl-fortimicin-4,5-carbamate(5)

A magnetically stirred suspension of 0.8200 g of 2',6'-di-N-benzyloxycarbonylfortimicin B-1,2:4,5-bis-carbamate(4), 0.5158 g of sodium bicarbonate and 42 ml of methanol is heated under reflux for 2 hours. The methanol is evaporated under reduced pressure and the residue shaken with a mixture of 200 ml of 5% aqueous sodium bicarbonate and 100 ml of methanol. The methanol solution is separated and washed with 200 ml of 5% aqueous sodium chloride solution. The aqueous solutions are washed in series with two 50 ml portions of chloroform. The chloroform solutions are combined and dried over magnesium sulfate. Evaporation of the chloroform under reduced pressure leaves 0.8610 g of 1-N-methoxycarbonyl-2',6'-di-N-benzyloxycarbonyl-fortimicin B-4,5-carbamate(5):$[\alpha]_D^{24}$ −7.8° (c 1%, CH$_3$OH); NMR(CDCl$_3$)$\delta$1.12d(J=6.5 Hz)(C$_6'$—CH$_3$). 2.84(NCH$_3$), 3.45(OCH$_3$), 3.63(OCO$\underline{CH}_3$); IR(CDCl$_3$) 3563, 3438, 1755, 1706 cm$^{-1}$.

EXAMPLE 6

2',6'-Di-N-benzyloxycarbonylfortimicin B-4,5-carbamate(6)

A magnetically stirred mixture of g of 2',6'-di-N-benzyloxycarbonylfortimicin B-1,2:4,5-bis-carbamate(4), 10 ml of 2 N aqueous sodium hydroxide and 30 ml of 1,2-dimethoxyethane is heated under reflux for 2.7 hours. The resulting mixture is shaken with a mixture of 150 ml of chloroform and 200 ml of a saturated sodium chloride solution. The chloroform solution is separated and triturated with 200 ml of saturated sodium chloride solution. The aqueous solutions are washed with three 100 ml portions of chloroform. The chloroform solutions are combined and dried over magnesium sulfate. Evaporation of the chloroform under reduced pressure leaves 0.887 grams of product as a glass. Chromatography of the latter(0.824 g) on a column of silica gel packed and eluted with a solvent system composed of chloroform-methanol-ammonium hydroxide(conc.) [17.9:1.2:0.1(v/v/v)] gives 0.410 g of product(6):NMR(CDCl$_3$) $\delta$1.16d(J=6.5 Hz)(C$_6'$—CH$_3$),2,82(NCH$_3$), 3.46(OCH$_3$); IR (CDCl$_3$) 3568, 3446, 1752, 1702 cm$^{-1}$.

EXAMPLE 7

Fortimicin B-4,5-carbamate trihydrochloride 1,2',6'-Tri-N-benzyloxycarbonylfortimicin B-4,5-carbamate(3)(400 mg) in 35 ml of 0.2 N hydrochloric acid in methanol is hydrogenated under 3 atmospheres of hydrogen for 4 hours in the present of 400 mg of 5% palladium on carbon. The catalyst is removed by filtration and the methanol evaporated under reduced pressure. Residual hydrochloric acid is removed by co-distillation with methanol under reduced pressure leaving 244 g of product as a glass:$[\alpha]_D^{22}$+12° (c 1%,CH$_3$OH); NMR(D$_2$O)$\delta$ 1,79d (J=6.4 Hz), 3.33(NCH$_3$),4.00(OCH$_3$), 6.12d(J=4.8 Hz)(C$_1$—Hz); IR(KBr) 1744 cm$^{-1}$.

EXAMPLE 8

2',6'-Di-N-benzyloxycarbonylfortimicin B-1,2;4,5-Biscarbamate (4)

A solution prepared from 5.36 g of 4N-ethoxycarbonyl-2',6'-di-N-benzyloxycarbonylfortimicin B-1,2-carbamate, 5.61 g of 1,5-diazabicyclo [5.4.0] undecene-5, and 250 ml of benzene was heated under reflux for 6 hours and then allowed to stand overnight at ambient temperature. Water (100 ml) was added and the resulting solution was stirred at room temperature for 1 hr. The resulting mixture was shaken with 300 ml of CHCl$_3$. The organic phase was separated and washed with two 200-ml portions of saturated NaCl solution and dried (MgSO$_4$). Evaporation of the solvent under reduced pressure left 5.19 g of crude 9. Chromatography of the latter on a column of 450 g of silica gel prepared and eluted with a solvent system prepared from 1,2-dichloroethanemethanol [10:1 (v/v)] gave 1.49 g of 2',6'-di-N-benzyloxycarbonylfortimicin B-1,2;4,5-biscarbamate identical with that prepared in example 4.

EXAMPLE 9

1-N-Methoxycarbonyl-2',6'-di-N-benzyloxycarbonylfortimicin B-4,5-carbamate (5)

To a magnetically stirred solution of 0.2645 g of 2',6'-di-N-benzyloxycarbonylfortimicin B-4,5-carbamate (6), 0.463 g of NaHCO$_3$, 14 ml of CH$_3$OH, and 2 ml of water is added 0.12 ml of methoxycarbonyl chloride. Stirring is continued at ambient temperature for 3.5 hr. The resulting suspension is shaken with a mixture of CHCl$_3$ and 5% aqueous NaHCO$_3$. The CHCl$_3$ solution is separated and dried (MgSO$_4$). Evaporation of the CHCl$_3$ under reduced pressure leaves 0.2665 of 5 identical with that prepared as described in example 5 above.

We claim:

1. A fortimicin B-4,5-carbamate represented by the formula:

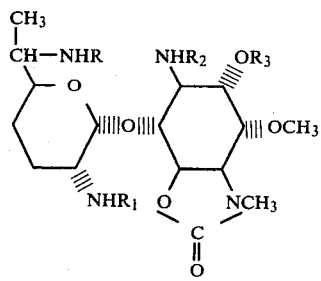

wherein R is hydrogen or monocyclearyloxy carbonyl; R$_1$ is hydrogen or an amine-protecting group; R$_2$ is hydrogen or loweralkyloxycarbonyl; and R$_3$ is hydrogen and when R, R$_1$ or R$_2$ are hydrogen, the salts thereof.

2. A compound of claim 1 wherein R and R$_1$ each are benzyloxycarbonyl.

3. A compound of claim 2 wherein R$_2$ is loweralkoxycarbonyl.

4. A compound of claim 2 wherein R$_2$ is hydrogen.

5. 1-N-Methoxycarbonyl-2',6'-di-N-benzyloxycarbonylfortimicin B-4,5-carbamate.

6. 2',6'-Di-N-benzyloxycarbonylfortimicin B-4,5-carbamate or a salt thereof.

7. Fortimicin B-4,5-carbamate or a salt thereof.

* * * * *

UNITED STATES PATENT AND TRADEMARK OFFICE
CERTIFICATE OF CORRECTION

PATENT NO. : 4,275,193
DATED : June 23, 1981
INVENTOR(S) : John S. Tadanier and Jerry R. Martin It is certified that error appears in the above—identified patent and that said Letters Patent is hereby corrected as shown below:

In column 8, line 19, delete "monocyclearyloxy" and insert - - monocyclicaryloxy- - .

In column 8, line 20, delete "an amine protecting group"

and insert - - monocyclicaryloxy - - .

Signed and Sealed this

Second Day of February 1982

[SEAL]

Attest:

GERALD J. MOSSINGHOFF

Attesting Officer   Commissioner of Patents and Trademarks